United States Patent
Fayolle et al.

(10) Patent No.: US 6,849,445 B2
(45) Date of Patent: Feb. 1, 2005

(54) PROCESS FOR TREATMENT OF AQUEOUS EFFLUENTS THAT CONTAIN METHYL-TERT-BUTYL ETHER AND/OR METHYL-TERT-AMYL ETHER BY *MYCOBACTERIUM AUSTROAFRICANUM* I-2562

(75) Inventors: Françoise Fayolle, Clamart (FR); Alan Francois, Soisy S/Montmorency (FR); Frédéric Monot, Nanterre (FR)

(73) Assignee: Institut Francois du Petrole, Rueil Malmaison (FR)

( * ) Notice: Subject to any disclaimer, the term of this patent is extended or adjusted under 35 U.S.C. 154(b) by 122 days.

(21) Appl. No.: 10/269,869

(22) Filed: Oct. 15, 2002

(65) Prior Publication Data

US 2003/0073225 A1 Apr. 17, 2003

(30) Foreign Application Priority Data

Oct. 15, 2001 (FR) .......................................... 01 13299

(51) Int. Cl.[7] .............................. B09B 3/00; C12N 1/00
(52) U.S. Cl. ..................................... 435/262.5; 435/863
(58) Field of Search ................................ 435/262.5, 863

(56) References Cited

U.S. PATENT DOCUMENTS 5,814,514 A  9/1998 McClay et al.

FOREIGN PATENT DOCUMENTS

| WO | 00 63343 | 10/2000 |
|---|---|---|
| WO | 01 34528 | 5/2001 |

OTHER PUBLICATIONS

SolanoSerena, F. et al. A Mycobacterium strain with extended capacities for degradation of gasoline hydrocarbons. Jun. 2000 Applied and Environmental Microbiology, vol. 66, No. 6, pp. 2392–2399.*

* cited by examiner

*Primary Examiner*—David A. Redding
(74) *Attorney, Agent, or Firm*—Millen White Zelano & Branigan, P.C.

(57) ABSTRACT

A process for treatment of aqueous effluents, for example, an aquifer, that contains at least methyl-tert-butyl ether (MTBE) or methyl-tert-amyl ether (TAME) so as to reduce the concentration of said ether is described, characterized in that a *Mycobacterium austroafricanum* I-2562 bacterium is grown under aerobic conditions in the presence of a growth substrate that contains said ether, and said ether is degraded by said bacterium down to the final degradation products, carbon dioxide and water. The results are improved in the presence of yeast extract.

19 Claims, 3 Drawing Sheets

PROCESS FOR TREATMENT OF AQUEOUS EFFLUENTS THAT CONTAIN METHYL-TERT-BUTYL ETHER AND/OR METHYL-TERT-AMYL ETHER BY *MYCOBACTERIUM AUSTROAFRICANUM* I-2562

The invention relates to microorganisms that are able to degrade methyl-tert-butyl ether and/or tert-amyl-methyl ether.

It pertains in particular to the water treatment industry.

It is known that methyl-tert-butyl ether or methyl-tert-amyl ether—designated below respectively under the terms of MTBE and TAME—is one of the ethers that can be used as an oxidized additive in unleaded gasolines for the purpose of increasing their octane number. The increasing use of additives such as MTBE or TAME brings about large stored and transported volumes, mixed in gasolines in particular. It is therefore necessary to know what becomes of this compound in the case of accidental dumping leading to ground, groundwater or surface pollution. MTBE or TAME is an ether that is produced by the condensation of methanol respectively on isobutene or isopentene. Its structure, which comprises an ether bond as well as a tertiary carbon, is such as to make it resistant to the biodegradation by microorganisms that are present in the environment.

Recent literature relative to the biodegradation of alkyl ethers used in the gasolines indicates that the metabolism of these compounds in the environment is not a common phenomenon and that it is relatively slow, under both aerobic conditions as well as anaerobic conditions.

The prior art is illustrated by Patent WO-0134528 and by the following patents:

U.S. Pat. No. 5,814,514 describes the use of bacterial colonies that use propane or isopropanol as a carbon-containing growth substrate (whereby the latter is oxidized), whereby the ethers are degraded by co-metabolism. In this patent, propane (or isopropanol) is introduced into the medium from the outside with the ether that is to be degraded, Patent WO-00/63 343 teaches a pure Rhodococcus culture (culture A) that can degrade the MTBE that is used as a carbon-containing growth substance. The Table and the Figure presented on page 22 of the patent show the degrees of homology with other colonies, classified by decreasing order. "Culture A" has high levels of similarity with *Rhodococcus* colonies and lower levels of similarity with the *Mycobacterium* colonies that are cited. The *Mycobacterium* colonies are mentioned here by way of comparison to show precisely that "culture A" is a *Rhodococcus* and not a *Mycobacterium*.

In Patent FR-A-2,787,783, the applicant isolated and described a bacterium, *Gordonia terrae* I-2194, for its capacity to grow on ETBE as a source of carbon and energy. This bacterium degraded ETBE into tert-butanol (TBA). This bacterium also proved capable of degrading MTBE in the presence of a carbon-containing growth substrate. Nevertheless, whether the compound that is to be degraded is ETBE or MTBE, TBA was formed in the growth medium. A second bacterium was therefore to be used for a total purification of effluents to be treated. Three different bacteria were isolated and are able to grow on TBA as a source of carbon and energy. These are, according to Patent FR-A-2, 800,748, *B. cepacia* I-2052, *Alcaligenes austroafricanum* I-2561, and *Mycobacterium austroafricanum* I-2562.

It is evident from this that it is necessary to find and identify new microorganisms that can biodegrade MTBE or TAME and to study their implementation in water treatment processes that allow significant reduction of residual concentrations of MTBE or TAME of urban or industrial waste water or contaminated aquifer layers, designated under the general name of effluents, contaminated by this product.

One of the new bacteria that was isolated by the applicant and that allows tert-butanol (TBA) in solution to degrade in water, *Mycobacterium austroafricanum* I-2562, has proven capable of also degrading MTBE in solution in water. A noteworthy fact is that *Mycobacterium austroafricanum* I-2562 can use MTBE as a sole source of carbon and energy.

One of the objectives of the invention is to describe the new potentialities of this bacterium that can degrade MTBE or TAME that is contained in solution in water so that it is used for treatment of polluted water.

In a more detailed manner, the invention relates to a new bacterial colony, isolated from the environment, that can degrade MTBE and/or TAME completely without an intermediate degradation product accumulating. This new bacterium that is deposited on Sep. 19, 2000 at the Pasteur Institute (CNCM of the Pasteur Institute, 25, rue du Docteur Roux, F-75724 PARIS CEDEX 15) is *Mycobacterium* sp. I-2562, subsequently identified as being *Mycobacterium austroafricanum* I-2562.

More specifically, the invention describes a process for treatment of aqueous effluents that contain at least one ether of the methyl-tert-butyl ether (MTBE) group or of the methyl-tert-amyl ether (TAME) group so as to reduce the concentration of said ether, characterized in that a *Mycobacterium austroafricanum* I-2562 is grown under aerobic conditions in the presence of a growth substrate that contains said ether as a sole source of carbon and energy, and said ether is degraded by said bacterium down to the final degradation products, carbon dioxide and water.

The intermediate degradation products of MTBE and TAME, respectively in particular tert-butanol (TBA) and tert-amyl alcohol (TAA), are also totally mineralized.

According to a characteristic of the invention, the aqueous effluents can be an aquifer that contains at least MTBE and/or TAME and in which the *Mycobacterium austroafricanum* I-2562 bacterium is introduced in a suitable form so as to reduce the concentration of MTBE and/or TAME in the aquifer.

According to another characteristic, it is possible to add yeast extract in proportions between 10 and 200 mg/l to the growth substrate.

The bacterium was isolated from activated sludges collected at a purification plant for urban waste water that was treated according to techniques for enrichment of specific microorganisms.

The resulting bacterial colony was isolated after specific enrichment in tert-butanol (TBA) or tert-amyl alcohol and tested in pure culture for its capacity to degrade MTBE or TAME.

In these experiments, it should be noted that MTBE or TAME can be provided as a sole source of carbon, but nutritional additives can be added to the growth medium to accelerate the growth in MTBE or in TAME of this new bacterium. High concentrations of MTBE and/or TAME, for example at most equal to 2 g/l, are degraded by the new bacterium at levels that can go up to 100%. *Mycobacterium austroafricanum* I-2562 is also able to degrade lower concentrations of MTBE or TAME. Excellent results were obtained with MTBE or TAME concentrations in the aqueous effluent of between 0.05 mg/l and 200 mg/l.

The use of these bacteria for continuous treatment of effluents polluted by MTBE and/or TAME can be carried out, for example, in a biofilter where the bacteria are attached on a mineral or organic substrate or else they can be added as an inoculum to purification plant sludges or in any other system that is adapted to water and ground treatment (biobarrier). More specifically, it is possible to make the bacterium develop in a biofilter system or biobarrier system with a suitable volume: the effluents that contain said ether are introduced in the presence of air or oxygen into the biofilter or into the biobarrier with a feed flow of MTBE and/or TAME that is less than 30 mg/l of biofilter and per hour, and the effluent is drawn off with a low concentration of said ether.

The invention will be better understood by the following examples that are given by way of illustration as well as by the figures, among which:

EXAMPLE 1

Growth of *Mycobacterium austroafricanum* I-2562 on a Mineral Medium in the Presence of MTBE as a Sole Source of Carbon A preculture of the *Mycobacterium austroafricanum* I-2562 bacterium is carried out: the *Mycobacterium austroafricanum* I-2562 colony is inoculated in a saline mineral medium MM that is supplemented with tert-butanol or TBA with 1 g/l as a source of carbon and energy. Medium MM has the following composition:

| | |
|---|---|
| $KH_2PO_4$ | 1.4 g |
| $K_2HPO_4$ | 1.7 g |
| $NaNO_3$ | 1.5 g |
| $MgSO_4$, 7 $H_2O$ | 0.5 g |
| $CaCl_2$, 2 $H_2O$ | 0.04 g |
| $FeCl_3$, 6 $H_2O$ | 0.012 g |
| Concentrated solution of vitamins | 1 ml |
| Concentrated solution of oligoelements | 1 ml |
| $H_2O$ | quantity sufficient for 1 liter |

The concentrated solution of vitamins has the following composition for 1 liter of distilled water:

| | |
|---|---|
| Biotin | 200 mg |
| Riboflavin | 50 mg |
| Nicotinamic acid | 50 mg |
| Pantothenate | 50 mg |
| p-Aminobenzoic acid | 50 mg |
| Folic acid | 20 mg |
| Thiamine | 15 mg |
| Cyanocobalamine | 1.5 mg |

The concentrated solution of oligoelements has the following composition for 1 liter of distilled water:

| | |
|---|---|
| $CuSO_4$, 5 $H_2O$ | 0.1 g |
| $MnSO_4$, 2 $H_2O$ | 1 g |
| $ZnSO_4$, 7 $H_2O$ | 1 g |
| $AlCl_3$, 6 $H_2O$ | 0.4 g |
| $NiCl_2$, 6 $H_2O$ | 0.25 g |
| $H_3BO_3$ | 0.1 g |
| $CoCl_2$, 6 $H_2O$ | 1 g |
| $Na_2MoO_4$, 2 $H_2O$ | 1 g |
| $Na_2WO_4$, 2 $H_2O$ | 1 g |

After growth, this preculture is centrifuged, washed with medium MM to remove any trace of residual TBA, and the bacterial cap that is thus obtained is used to inoculate 50 ml of medium MM to which MTBE is added at a final concentration of about 70 mg/l in an Erlenmeyer flask with a capacity of 500 ml that is closed with a Teflon-coated plug to avoid any loss of MTBE during the growth. Sampling is done at time t=O for a measurement of optical density at 600 nm ($O.D._{600\ nm}$) and an initial MTBE metering by gas chromatography (GC) analysis. The flask is then incubated at 30° C. in a rotary stirring mechanism. A sampling for the measurement of $O.D._{600\ nm}$ as well as a metering of the substrate and its possible degradation products is carried out at regular intervals. When all of the initial MTBE has been consumed, a second addition of MTBE is carried out at t=80 hours, and only the tracking of the measurement of the $O.D._{600\ nm}$ is then done in this second part of the experiment.

Figure 1:
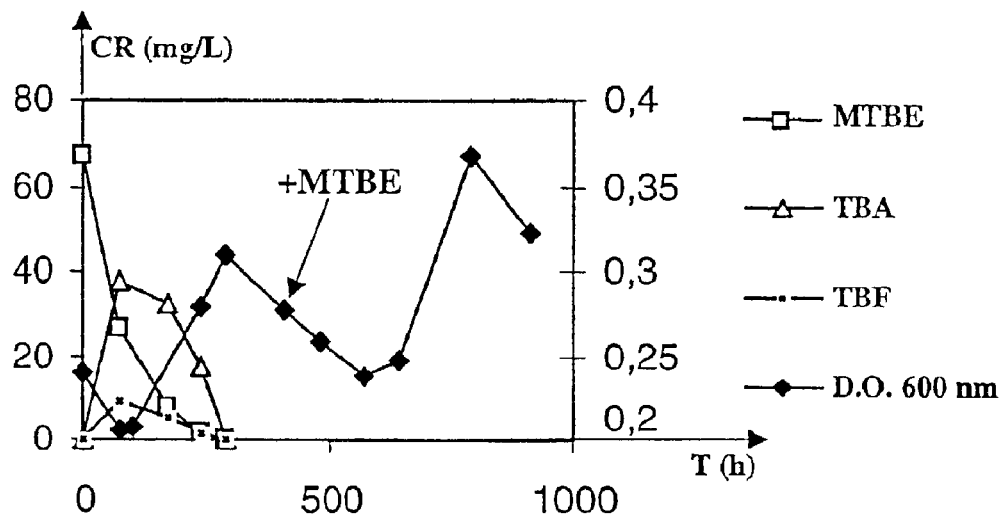
FIG. 1 illustrates the growth of *Mycobacterium austroafricanum* I-2562 on a mineral medium in the presence of MTBE as a sole source of carbon.

The result of this experiment is exhibited in FIG. 1, which shows on the ordinate the residual concentration in mg/l of three components (MTBE, TBA, TBF) as well as the optical density as a function of time on the abscissa.

As is seen in this figure, the first addition of MTBE is reflected by a growth of the *Mycobacterium austroafricanum* I-2562 bacterium. The MTBE is degraded in part in tert-butyl formate (TBF) and in tert-butyl alcohol (TBA). These two compounds are then used as a growth substrate, and an increase in the O.D. is obtained during their consumption. When there is no longer carbon-containing compound, the O.D. decreases slightly, and this is routinely observed at the end of the growth of bacteria. A second addition of MTBE then allows a resumption of the growth. This example shows well that *Mycobacterium austroafricanum* I-2562 uses the MTBE as a sole source of carbon and energy. No other carbon-containing substrate is necessary. The accumulated intermediate products are then themselves degraded. The mineralization of the MTBE can therefore take place without the presence of another carbon-containing substrate from an external source and in the absence of another colony that degrades TBA and TBF.

EXAMPLE 2

Effect of the Addition of Yeast Extract on the Growth of *Mycobacterium austroafricanum* I-2562 on MTBE as a Sole Source of Carbon It was desired to test whether the addition of a small amount of yeast extract in the culture medium could make possible a faster use of the MTBE provided as a sole source of carbon to *Mycobacterium austroafricanum* I-2562.

Figure 2:
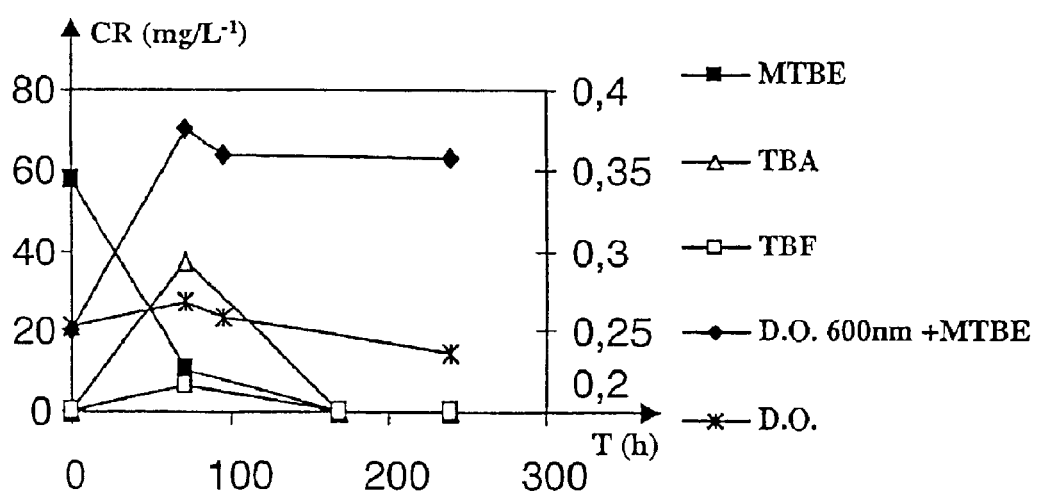
FIG. 2 shows the effect of the addition of yeast extract on the growth of *Mycobacterium austroafricanum* I-2562 on MTBE as a sole source of carbon.

A preculture of the *Mycobacterium austroafricanum* I-2562 bacterium is carried out under the same conditions as those described in Example 1. 50 ml of medium MM that contains yeast extract at a final concentration of 100 mg/l is prepared in an Erlenmeyer flask with a threaded and Teflon-coated plug, and MTBE is added at a concentration that is similar to the one described in Example 1. As described in Example 1, after the culture medium is inoculated, the growth and development of the substrate is followed. The result of this experiment is exhibited in FIG. 2, which shows, on the ordinate, the residual concentration in mg/l of the three components (MTBE, TBA, TBF) as well as the optical density with or without MTBE, as a function of time on the abscissa.

As is seen in this figure, and by comparison with the result of Example 1, the addition of a small amount of yeast extract makes it possible to increase the degradation rate of the MTBE. Whereas in the preceding example an incubation period of the culture of 288 hours was necessary to totally degrade the MTBE (i.e., the MTBE itself and its intermediate degradation products, which are TBF and TBA), a quite smaller duration, equal to 168 hours, is necessary in the presence of yeast extract to obtain the same result. It will be noted that, in the control of the experiment that consists of a flask of medium MM supplemented with the yeast extract at the same concentration as in the test (100 mg/l) inoculated with the *Mycobacterium austroafricanum* I-2562 colony but without the addition of MTBE, no growth is observed. This well proves that the growth of the *Mycobacterium austroafricanum* I-2562 bacterium is quite exclusively due to its capacity for growth on MTBE.

EXAMPLE 3

Growth of *Mycobacterium austroafricanum* I-2562 on Different Concentrations of MTBE in the Presence of Yeast Extract (100 mg.L$^{-1}$)

It was desired to test the growth capacities of the *Mycobacterium austroafricanum* I-2562 bacterium on higher concentrations of MTBE. The experiment is the same as the one described in Example 2, i.e., carried out on medium MM that is supplemented with the yeast extract at 100 mg/l. Three 1 l Erlenmeyer flasks with a Teflon-coated and threaded plug that contain 100 ml of medium MM supplemented with yeast extract are inoculated with a preculture prepared as in Example 1. MTBE at 200 mg/l or at 400 mg/l is added to two of these flasks. The third of these flasks does not contain MTBE and is the control of the experiment on the yeast extract alone. A sampling is carried out to measure the initial $O.D._{600\ nm}$.

These cultures are incubated at 30° C. in a rotary stirring mechanism. Samplings are taken regularly for the tracking of the growth by measurement of the $O.D._{600\ nm}$.

MTBE is then added at regular intervals to the culture medium at a rate of 100 mg/l.

Figure 3:
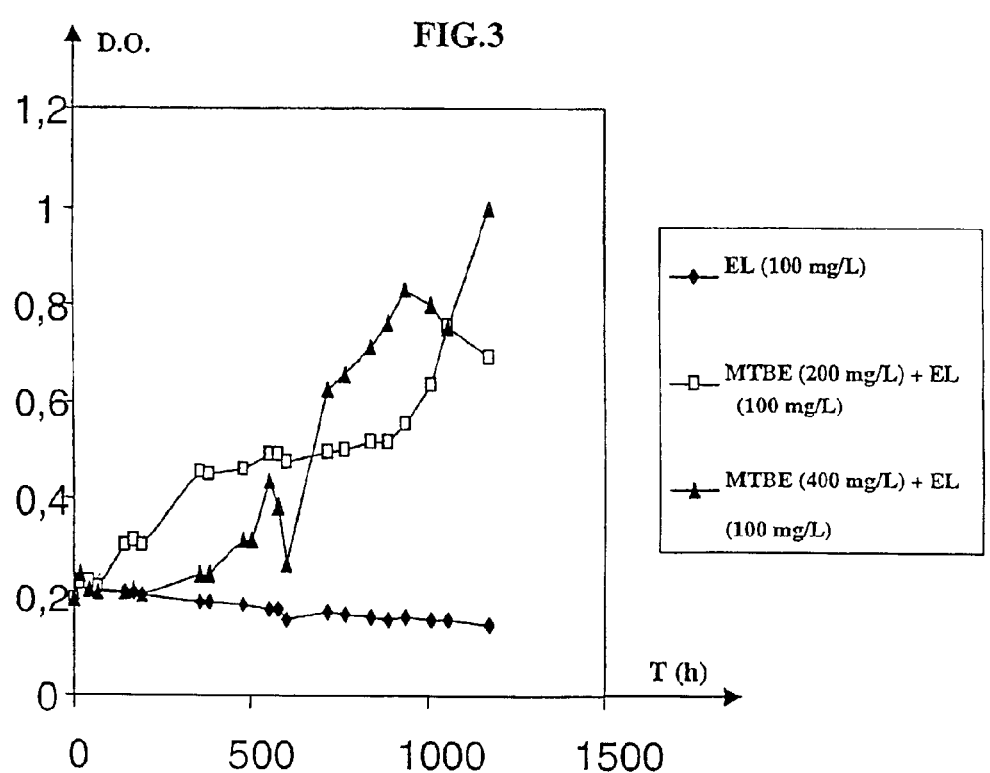
FIG. 3 shows the growth of *Mycobacterium austroafricanum* I-2562 on different high concentrations of MTBE in the presence of yeast extract (100 mg/l).

The result of this experiment is shown in FIG. 3, which represents on the ordinate the optical density at 600 nm at different concentrations of MTBE in the presence of yeast extract as a function of time in hours, on the abscissa as well as the optical density in the presence of yeast extract alone. In this figure, the successive additions of MTBE at 100 mg/l are represented by arrows. This curve shows that the growth is linked to the addition of MTBE in the culture medium.

In this figure, it is seen that the addition of higher concentrations is reflected by a latent period before growth, which is significant. It is one hundred hours at a concentration of MTBE of 200 mg/l and about 200 hours at a concentration of MTBE of 40 mg/l. Furthermore, it is significant that the *Mycobacterium austroafricanum* I-2562 colony is able to develop even at high concentrations of MTBE. As in Example 2, no growth on the yeast extract alone is observed.

EXAMPLE 4

Growth of *Mycobacterium austroafricanum* I-2562 on a Mineral Medium in the Presence of TAME as a Sole Source of Carbon A preculture of the *Mycobacterium austroafricanum* I-2562 bacterium is carried out: the *Mycobacterium austroafricanum* I-2562 colony is inoculated on a saline mineral medium MM2 that is supplemented with tert-butanol or TBA at 1 g.L$^{-1}$ as a source of carbon and energy. Medium MM2 has the following composition:

| | |
|---|---|
| $KH_2PO_4$ | 1.4 g |
| $K_2HPO_4$ | 1.7 g |
| $(NH_4)_2SO_4$ | 1.2 g |
| $MgSO_4, 7\ H_2O$ | 0.5 g |
| $CaCl_2, 2\ H_2O$ | 0.04 g |
| $FeCl_3, 6\ H_2O$ | 0.012 g |
| Yeast extract | 0.1 g |
| Concentrated solution of vitamins | 1 ml |
| Concentrated solution of oligoelements | 1 ml |
| $H_2O$ | quantity sufficient for 1 liter |

The concentrated solution of vitamins has the following composition for 1 liter of distilled water:

| | |
|---|---|
| Biotin | 200 mg |
| Riboflavin | 50 mg |
| Nicotinamic acid | 50 mg |
| Pantothenate | 50 mg |
| p-Aminobenzoic acid | 50 mg |
| Folic acid | 20 mg |
| Thiamine | 15 mg |
| Cyanocobalamine | 1.5 mg |

The concentrated solution of oligoelements has the following composition for 1 liter of distilled water:

| | |
|---|---|
| $CuSO_4, 5\ H_2O$ | 0.1 g |
| $MnSO_4, 2\ H_2O$ | 1 g |
| $ZnSO_4, 7\ H_2O$ | 1 g |
| $AlCl_3, 6\ H_2O$ | 0.4 g |
| $NiCl_2, 6\ H_2O$ | 0.25 g |
| $H_3BO_3$ | 0.1 g |
| $CoCl_2, 6\ H_2O$ | 1 g |
| $Na_2MoO_4, 2\ H_2O$ | 1 g |
| $Na_2WO_4, 2\ H_2O_2$ | 1 g |

After growth, this preculture is centrifuged, washed with medium MM2 to remove any trace of residual TBA, and the bacterial cap that is thus obtained is used to inoculate three 100-ml flasks of medium MM2 to which TAME is added at a final concentration of about 90 mg.L$^{-1}$ in Erlenmeyer flasks with capacities of 500 ml that are closed with Teflon-coated plugs to avoid any loss of TAME during the growth. A sampling is carried out at time t=0 for a measurement of optical density at 600 nm ($O.D._{600\ nm}$) and an initial TAME metering by gas chromatography (GC) analysis. The flasks are then incubated at 30° C. in a rotary stirring mechanism. A sampling for the measurement of $O.D._{600\ nm}$ as well as a metering of the substrate and its possible degradation products are carried out at regular intervals.

Figure 4:
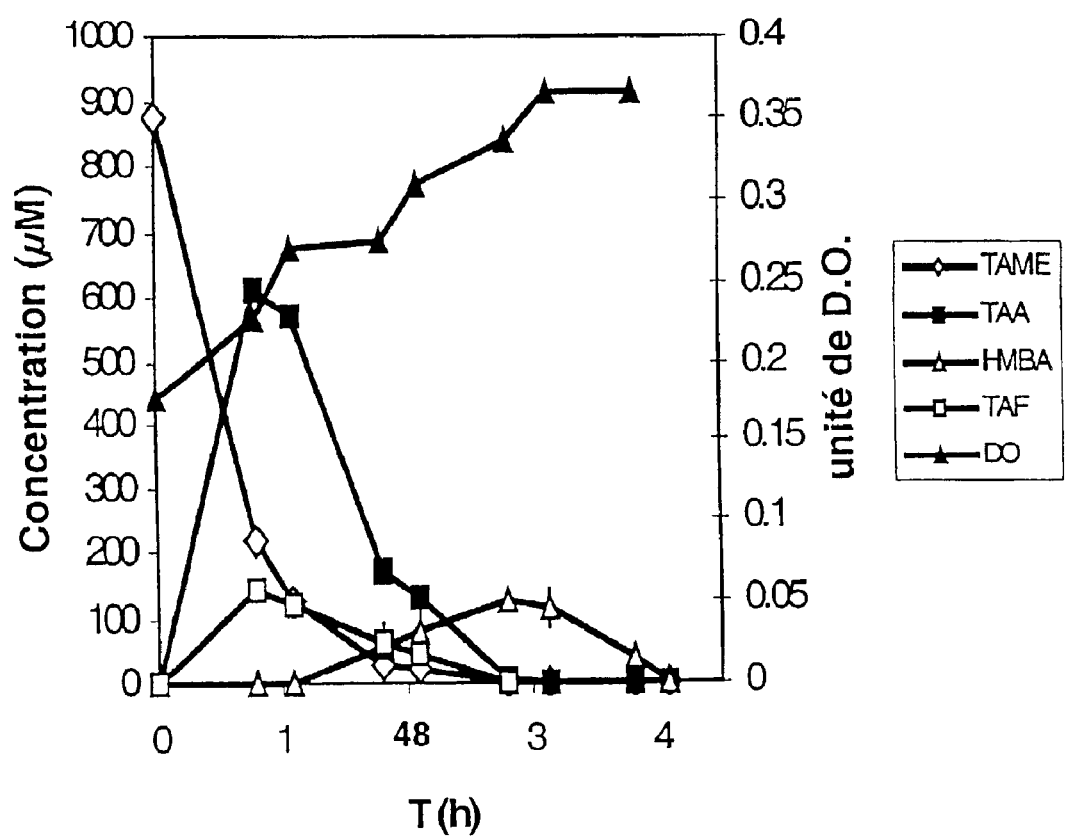
FIG. 4 illustrates the growth of the colony on TAME as a sole source of carbon.

The result of this experiment is exhibited in FIG. 4, which shows on the ordinate an average of residual concentrations in μM (micromol) of TAME and of three intermediate degradation products (tert-amyl formate or TAF, tert-amyl alcohol or TAA, and hydroxymethylbutyric acid or HMBA), as well as the optical density as a function of time, on the abscissa, expressed in hours.

As is seen in this figure, TAME is degraded in part in tert-amyl formate (TAF) and in tert-amyl alcohol (TAA). These two compounds are then used as a growth substrate, and it is possible to demonstrate the presence of hydroxymethylbutyric acid (HMBA), which is an intermediate product of the degradation of TAA. An increase in the O.D. is measured during the consumption of TAME and its metabolites. No other carbon-containing substrate is necessary. The accumulated intermediate products are then themselves degraded. The mineralization of the TAME can therefore take place without the presence of another carbon-containing substrate and in the absence of another colony that degrades TAF, TAA and HMBA.

What is claimed is:

1. Process for treatment of aqueous effluents that contain at least one ether of the methyl-tert-butyl ether (MTBE) group and the methyl-tert-amyl ester (TAME) group so as to reduce the concentration of said ether, characterized in that under aerobic condition, a *Mycobacterium austroafricanum* I-2562 bacterium is grown in the presence of a growth substrate that contains said ether as a source of carbon and energy, and said ether is degraded by said bacterium down to the final degradation products, carbon dioxide and water.

2. Process according to claim 1, wherein the aqueous effluents are an aquifer that contains at least MTBE and/or TAME and in which the *Mycobacterium austroafricanum* I-2562 bacterium is introduced in a suitable form so as to reduce the concentration of MTBE and/or TAME in the aquifer.

3. A process according to claim 1, wherein yeast extract, in proportions of between 10 and 200 mg/l, is added to the growth substrate.

4. A process according to claim 1, wherein the concentration of MTBE and/or TAME in the aqueous effluents that are to be treated is at most equal to 2 g/l.

5. A process according to claim 1, wherein said bacterium is developed in a biofilter system or a biobarrier system with a suitable volume; the effluents that contain said ether in the presence of air or oxygen are introduced into the biofilter or the biobarrier at a feed flow of MTBE and/or TAME that is less than 30 mg/l of biofilter and per hour; and the effluent is drawn off with a reduced concentration of said ether.

6. A process according to claim 1, wherein the concentration of MTBE and/or TAME in the aqueous effluents that are to be treated is between 0.05 mg/l and 200 mg/l.

7. A process according to claim 2, wherein yeast extract, in proportions of between 10 and 200 mg/l, is added to the growth substrate.

8. A process according to claim 4, wherein yeast extract, in proportions of between 10 and 200 mg/l, is added to the growth substrate.

9. A process according to claim 5, wherein yeast extract, in proportions of between 10 and 200 mg/l, is added to the growth substrate.

10. A process according to claim 6, wherein yeast extract, in proportions of between 10 and 200 mg/l, is added to the growth substrate.

11. A process according to claim 4, wherein the aqueous effluents are an aquifer that contains at least MTBE and/or TAME and in which the *Mycobacterium austroafricanum* I-2562 bacterium is introduced in a suitable form so as to reduce the concentration of MTBE and/or TAME in the aquifer.

12. A process according to claim 5, wherein the aqueous effluents are an aquifer that contains at least MTBE and/or TAME and in which the *Mycobacterium austroafricanum* I-2562 bacterium is introduced in a suitable form so as to reduce the concentration of MTBE and/or TAME in the aquifer.

13. A process according to claim 6, wherein the aqueous effluents are an aquifer that contains at least MTBE and/or TAME and in which the *Mycobacterium austroafricanum* I-2562 bacterium is introduced in a suitable form so as to reduce the concentration of MTBE and/or TAME in the aquifer.

14. A process according to claim 7, wherein the aqueous effluents are an aquifer that contains at least MTBE and/or TAME and in which the *Mycobacterium austroafricanum* I-2562 bacterium is introduced in a suitable form so as to reduce the concentration of MTBE and/or TAME in the aquifer.

15. A process according to claim 8, wherein the aqueous effluents are an aquifer that contains at least MTBE and/or TAME and in which the *Mycobacterium austroafricanum* I-2562 bacterium is introduced in a suitable form so as to reduce the concentration of MTBE and/or TAME in the aquifer.

16. A process according to claim 9, wherein the aqueous effluents are an aquifer that contains at least MTBE and/or TAME and in which the *Mycobacterium austroafricanum* I-2562 bacterium is introduced in a suitable form so as to reduce the concentration of MTBE and/or TAME in the aquifer.

17. A process according to claim 10, wherein the aqueous effluents are an aquifer that contains at least MTBE and/or TAME and in which the *Mycobacterium austroafricanum* I-2562 bacterium is introduced in a suitable form so as to reduce the concentration of MTBE and/or TAME in the aquifer.

18. A process according to claim 1, wherein at least one of MTBE or TAME is the sole source of energy.

19. A process according to claim 1, wherein I-2562 is isolated from the environment of *Mycobacterium* sp. I-2562.

* * * * *